(12) United States Patent
Malinda et al.

(10) Patent No.: US 6,197,751 B1
(45) Date of Patent: Mar. 6, 2001

(54) THYMOSIN α1 PROMOTES TISSUE REPAIR, ANGIOGENESIS AND CELL MIGRATION

(75) Inventors: Katherine M. Malinda, Millersville; Hynda K. Kleinman, Kensington, both of MD (US); Allan L. Goldstein, Washington, DC (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/186,476

(22) Filed: Nov. 4, 1998

Related U.S. Application Data
(60) Provisional application No. 60/069,590, filed on Dec. 12, 1997, and provisional application No. 60/065,032, filed on Nov. 10, 1997.

(51) Int. Cl.[7] .................................................. A61K 38/17
(52) U.S. Cl. ................................. 514/21; 514/12
(58) Field of Search .................... 435/29; 514/12, 514/21; 530/324, 351

(56) References Cited

U.S. PATENT DOCUMENTS

| | | | |
|---|---|---|---|
| 4,650,674 | * 3/1987 | Aggarwal et al. | 514/12 |
| 5,308,833 | * 5/1994 | Scharschmidt et al. | 514/12 |
| 5,468,737 | 11/1995 | McAnalley et al. | 514/54 |
| 5,514,555 | 5/1996 | Springer et al. | 435/7.24 |
| 5,556,645 | 9/1996 | Bockman et al. | |
| 5,574,026 | 11/1996 | Backer et al. | 514/152 |
| 5,585,352 | * 12/1996 | Goldstein et al. | 514/12 |
| 5,629,292 | 5/1997 | Rodgers et al. | 514/16 |
| 5,632,983 | * 5/1997 | Hadden | 424/85.1 |
| 5,686,425 | 11/1997 | Lee et al. | 514/21 |

OTHER PUBLICATIONS

Frillings et al. Appearance of Thymosin 1 in Supernatants . . . Arch. Biochem. Biophys. vol. 296, No. 1, pp. 256–263, Jul. 1992.*

Frohm et al., "Biochemical and antibacterial analysis of human wound and blister fluid" *Eur. J. Biochem.*, 237, 86–92, 1996.

Grant et al., "Matrigel induces thymosin β4 gene in differentiating endothelial cells" *Journal of Cell Science*, 108, 3685–3694, 1995.

Malinda et al., "Thymosin β4 stimulates directional migration of human umbilical vein endothelial cells" *Thyomosin β4, Enhances Endothelial Cell Migration*, 474–481, 1997.

* cited by examiner

*Primary Examiner*—Jeffrey E. Russel
(74) *Attorney, Agent, or Firm*—Fish & Richardson P.C.

(57) ABSTRACT

The present invention relates to methods for promoting tissue repair, angiogenesis and cell migration. The method of the invention utilizes thymosin α1 (Tα1) peptide to promote tissue repair, angiogenesis and cell migration. The invention further relates to modulating Tα1 activity in tissues.

16 Claims, 6 Drawing Sheets

THYMOSIN α1 PROMOTES TISSUE REPAIR, ANGIOGENESIS AND CELL MIGRATION

RELATED APPLICATIONS

This applications claims priority from U.S. Provisional Patent Application Ser. No. 60/069,590 filed Dec. 12, 1997 and U.S. Provisional Patent Application Ser. No. 60/065,032 filed Nov. 10, 1997.

TECHNICAL FIELD

The present invention relates generally to tissue repair and more specifically to methods for regulating wound healing, angiogenesis and cell migration using thymosin α1 (Tα1).

BACKGROUND

Impaired tissue healing is a significant problem in health care. Chronic, non-healing wounds are a major cause of prolonged morbidity in the aged human population. This is especially the case in bedridden or diabetic patients who develop severe, non-healing skin ulcers. In many of these cases, the delay in healing is a result of inadequate blood supply either as a result of continuous pressure or of vascular blockage. Poor capillary circulation due to small artery atherosclerosis or venous stasis contribute to the failure to repair damaged tissue. Such tissues are often infected with microorganisms that proliferate unchallenged by the innate defense systems of the body which require well vascularized tissue to effectively eliminate pathogenic organisms. As a result, most therapeutic intervention centers on restoring blood flow to ischemic tissues thereby allowing nutrients and immunological factors access to the site of the wound.

Wounds (i.e., lacerations or openings) in mammalian tissue result in tissue disruption and coagulation of the microvasculature at the wound face. Repair of such damage represents an orderly, controlled cellular response to injury. All soft tissue wounds, regardless of size, heal in a similar manner. Tissue growth and repair are biologic systems wherein cellular proliferation and angiogenesis occur.

Although many of the basic biochemical steps in wound healing have been characterized, a number of key regulatory factors have yet to be identified. The identification of such factors could lead to improved methods for the treatment of disease states associated with ineffectual wound healing. In wound healing, lymphoid cells release soluble factors that attract fibroblasts and macrophages initiating repair, endothelial cell migration, angiogenesis and matrix production.

An important aspect of wound repair is the revascularization of damaged tissue by angiogenesis. The process of angiogenesis involves endothelial cell attachment, basement membrane degradation and synthesis, migration and proliferation. Mitogenic factors released from lymphoid and endothelial cells can induce angiogenesis and promote neovascularization of damaged tissue. Regulation of angiogenesis is of considerable significance in tissue formation, wound healing and in pathological conditions such as cancer, Wegener's granuloma, Takayasu's arteritis, systemic lupus erythematosus and other autoimmune diseases.

Previous studies have used the "scratch" wound closure assay to assess the potential effects of an agent on in vitro cell migration. Though informative, such a test does not mimic in vivo wound healing conditions to the extent that all factors involved in wound closure are present in the assay. For this reason, in vivo systems have been developed to assess the ability of an agent or factor to modulate wound healing activities.

Tα1 was initially identified as an immunomodulatory factor which affects T-cell maturation, differentiation and function in vitro and in vivo. Tα1 can enhance the production of IL-2 and a-IFN and upregulate the expression of IL-2 receptors on mitogen-stimulated T-cells. In addition, Tα1 has important actions outside the immune system related to a role for this peptide and its 113 amino acid parent molecule, prothymosin α, in regulating cell proliferation and apoptosis (Sburlati et al., Proc. Natl. Acad. Sci. 88:253, 1991).

SUMMARY OF THE INVENTION

The present invention is based on the discovery that thymosin α1 (Tα1) accelerates wound healing and stimulates angiogenesis. The invention is further based on the discovery that Tα1 enhances the morphological differentiation of endothelial cells and is a potent chemoattractant for endothelial cells and monocytes.

In a first embodiment, the invention provides a method for accelerating wound healing in a subject in need of such treatment including contacting the site of the wound with a therapeutically effective amount of a composition containing thymosin α1 peptide.

In another embodiment, the invention provides a method for modulating angiogenesis in a tissue including contacting the tissue with a therapeutically effective amount of a composition containing thymosin α1 peptide.

In another embodiment, the invention provides a method of inhibiting angiogenesis in a subject, including administering to the subject a composition containing an agent which regulates thymosin α1 activity.

In yet another embodiment, the invention provides a method of diagnosing a pathological state in a subject suspected of having pathology characterized by a cell proliferative disorder associated with thymosin α1, including obtaining a sample suspected of containing thymosin α1 from the subject, determining the level of thymosin α1 in the sample and comparing the level of thymosin α1 in the sample to the level of thymosin α1 in a normal standard sample.

In another embodiment, the invention provides a method for ameliorating a cell proliferative disorder associated with thymosin α1, including treating a subject having the disorder, at the site of the disorder, with a composition which regulates thymosin α1 activity.

DETAILED DESCRIPTION OF THE INVENTION

The present invention arose from an investigation of the effects of Tα1 on cell differentiation and on cell migration. In vitro results demonstrate that Tα1 enhances the formation of tube-like structures by human umbilical vein epithelial cells (HUVECs) cultured on Matrigel. Additional experiments demonstrate that Tα1 acts as a chemoattractant to stimulate directional HUVEC migration. Boyden chamber assays with a variety of cell types demonstrate that migratory stimulation occurs specifically with endothelial cells and monocytes. Tα1 stimulates cell migration in vivo using subcutaneously implanted Matrigel and stimulates wound healing when applied topically or injected intraperitoneally in a rat wound model.

The present invention identifies Tα1 as active in promoting endothelial cell migration, angiogenesis and wound healing in vivo. In vivo plug results indicate that migration and angiogenesis are stimulated at or above the levels observed for migration and angiogenesis in response to the positive control epithelial cell growth stimulator (ECGS). Additionally, Tα1 accelerates wound healing in a punch wound assay. Complete reepitheliazation was observed with both intraperitoneal and topical applications of Tα1 and neovascularization was more extensive in treated wounds. Increased levels of collagen were also observed in treated wounds showing that Tα1 treatment can also accelerate wound contraction and stimulate the healing process.

The methods of the present invention results from the identification of the effect of thymosinα1 (Tα1) on wound healing, angiogenesis and cell migration. Tα1 enhances the morphological differentiation of endothelial cells and is a potent chemoattractant for endothelial cells and monocytes. In vivo, Tα1 stimulated angiogenesis in a subcutaneous model (see Example 6). When given either topically or intraperitoneally, Tα1 accelerated angiogenesis and promoted wound healing (see Example 7). Further, the present invention identifies a direct effect of Tα1 on monocyte migration (see Table 1).

Modulation of Tissue Regneration

In one embodiment, the invention provides a method for accelerating wound healing in a subject by applying to the wound a therapeutically effective amount of a composition which contains Tα1 peptides. Tα1 peptide is valuable as a therapeutic in cases in which there is impaired healing of skin wounds or there is a need to augment as, normal healing mechanisms.

Tα1 peptide was initially localized in the thymus but is also in other tissues. Therefore, agents which stimulate the production of Tα1 peptides can be added to a composition that is used to accelerate Tα1 production from such cells. In addition, agents which promote wound repair can further be included in such compositions to augment wound healing. Such agents include members of the family of growth factors such as insulin-like growth factor (IGF-I), platelet-derived growth factor (PDGF), epidermal growth factor (EGF), transforming growth factor beta (TGF-β) and basic fibroblast growth factor (bFGF). More preferably, the agent is transforming growth factor beta (TGF-β) or other member of the TGF-β superfamily. The Tα1 compositions of the invention aid in healing the wound, in part, by promoting the growth of connective tissue. The Tα1 compositions are prepared by combining, in any pharmaceutically acceptable carrier substance, e.g., inert gels or liquids, the purified Tα1 peptides of the invention.

As used herein, a "therapeutically effective amount" of a composition containing Tα1 for use in tissue repair is defined as that amount that is effective in promoting tissue regeneration. Diseases, disorders or ailments modulated by Tα1 include tissue repair subsequent to traumatic injuries or conditions including arthritis, osteoporosis and other skeletal disorders, and burns. Because these problems are due to a poor growth response of the fibroblasts, stem cells, chondrocytes, osteoblasts or fibroblasts at the site of injury, the addition of an active biologic agent that stimulates or induces growth of these cells is beneficial. The term "induce" or "induction" as used herein, refers to the activation, stimulation, enhancement, initiation and or maintenance of the cellular mechanisms or processes necessary for the formation of any of the tissue, repair process or development as described herein.

In another aspect, the invention is useful for revitalizing scar tissue resulting from injuries due to surgical procedures, irradiation, laceration, toxic chemicals, viral infection bacterial infection or burns. The term "scar tissue" means fibrotic or collagenous tissue formed during the healing of a wound or other morbid process. For example, Tα1 can be included in a controlled release matrix which can be positioned in proximity to damaged tissue thereby promoting regeneration and revascularization of such tissue. The term "controlled release matrix" means any composition which allows the slow release of a bioactive substance which is mixed or admixed therein. The matrix can be a solid composition, a porous material, or a semi-solid, gel or liquid suspension containing bioactive substances. The term "bioactive material" means any composition that will modulate tissue repair when used in accordance with the method of the present invention. The bioactive materials/matrix can be introduced by means of injection, surgery, catheters or any other means suitable for modulating tissue repair.

It is envisioned that the method of the invention can be used to aid wound repair in guided tissue regeneration (GTR) procedures. Such procedures are currently used by those skilled in the medical arts to accelerate wound healing following invasive surgical procedures. Typically, nonresorbable or bioabsorbable membranes are used to accelerate wound healing by promoting the repopulation of the wound area with cells which form the architectural and structural matrix of the tissue. For example, the method of the invention can be used in aiding periodontal tissue regeneration in a human or lower animal by placing a composition containing a bioresorbable polymer, leachable solvent, and Tα1 at a site in need of periodontal tissue regeneration in a human or other mammal such that the composition is effective for aiding tissue regeneration by releasing a therapeutically-effective amount of Tα1 at the site.

In another aspect, the invention can be useful for the purposes of promoting tissue growth during the process of tissue engineering. As used herein, "tissue engineering" is defined as the creation, design, and fabrication of biological prosthetic devices, in combination with synthetic or natural materials, for the augmentation or replacement of body tissues and organs. Thus, the present method can be used to augment the design and growth of human tissues outside the body for later implantation in the repair or replacement of diseased tissues. For example, Tα1 may be useful in promoting the growth of skin graft replacements which are used as a therapy in the treatment of burns.

In another aspect of tissue engineering, Tα1 of the present invention can be included in cell-containing or cell-free devices which induce the regeneration of functional human tissues when implanted at a site which requires regeneration. As previously discussed, biomaterial-guided tissue regeneration can be used to promote bone regrowth in, for example, periodontal disease. Thus, Tα1 can be used to promote the growth of reconstituted tissues assembled into three-dimensional configurations at the site of a wound or other tissue in need of such repair.

In another aspect of tissue engineering, Tα1 can be included in external or internal devices containing human tissues designed to replace the function of diseased internal tissues. This approach involves isolating cells from the body, placing them on or within structural matrices, and implanting the new system inside the body or using the system outside the body. The method of the invention can be included in such matrices to promote the growth of tissues contained in the matrices. For example, Tα1 can be included in a cell-lined vascular graft to promote the growth of the cells contained in the graft. It is envisioned that the method of the invention can be used to augment tissue repair, regeneration and engineering in products such as cartilage and bone, central nervous system tissues, muscle, liver, and pancreatic islet (insulin-producing) cells.

The present invention further provides a method for modulating female reproductive tract function. Growth factors have been shown to play a role in cyclic mitosis and differentiation of endometrial cellular components, recruitment of macrophages in decidualizing the endometrium, endometrial-trophoblast interactions, early pregnancy maintenance, and endometrial functional regeneration. The term "modulate" as used herein, denotes a modification of an existing condition or biologic state. Modulation of a condition as defined herein, encompasses both an increase or a decrease in the determinants affecting the existing condition. For example, administration of Tα1 could be used to augment uterine functions in a condition where the promotion of growth is desired. For example, the uterus may be treated with Tα1 to promote the growth and development of placental membranes or endometrial growth. Furthermore, treatment with Tat may be used to promote and maintain a pregnancy by facilitating endometrial-trophoblast interaction. Alternatively, antagonists to Tα1 could be administered to modulate conditions of excessive endometrial growth in which the level of Tα1 is excessive in comparison to a normal biologic condition.

Another therapeutic approach included within the invention involves direct administration of reagents or compositions including the Tα1 of the invention by any conventional administration technique (for example, but not restricted to, local injection, inhalation, or systemic administration), to a subject with a fibrotic, a scelortic, or a cell proliferative disorder such as, for example, atherosclerosis. Administration of Tα1, as described above, can accelerate wound healing, induce the formation of tissue repair or regeneration, or promote the growth and development of the endometrium. The reagent, formulation or composition may also be targeted to specific cells or receptors by any method described herein or by any method known in the art of delivering, targeting and expressing genes encoding Tα1. The actual dosage of reagent, formulation or composition that modulates a fibrotic disorder, a scelortic disorder, a cell proliferative disorder, atherosclerosis or wound healing depends on many factors, including the size and health of an organism. However, one of ordinary skill in the art can use the following teachings describing the methods and techniques for determining clinical dosages (Spilker B., *Guide to Clinical Studies and Developing Protocols,* Raven Press Books, Ltd., New York, 1984, pp. 7–13, 54–60; Spilker B., *Guide to Clinical Trials,* Raven Press, Ltd., New York, 1991, pp. 93–101; Craig C., and R. Stitzel, eds., *Modern Pharmacology,* 2d ed., Little, Brown and Co., Boston, 1986, pp. 127–33; T. Speight, ed., *Avery's Drug Treatment: Principles and Practice of Clinical Pharmacology and Therapeutics,* 3d ed., Williams and Wilkins, Baltimore, 1987, pp. 50–56; R. Tallarida, R. Raffa and P. McGonigle, *Principles in General Pharmacology,* Springer-Verlag, New York, 1988, pp. 18–20) or to determine the appropriate dosage to use.

In yet another embodiment, the invention may provide a method of diagnosing a pathological state in a subject suspected of having pathology characterized by a cell proliferative disorder assoicated with thymosin α1, including obtaining a sample suspected of containing thymosin α1 from the subject, determining the level of thymosin α1 in the sample and comparing the level of thymosinα1 in the sample to the level of thymosinα1 in a normal standard sample. Such conditions include but are not restricted to cell proliferative disorders, various fibrotic conditions including scleroderma, arthritis, liver cirrhosis, and uterine fibroids. For example, a sample suspected of containing Tα1 is obtained from a subject, the level of Tα1 peptide is determined and compared with the level of Tα1 peptide in a normal tissue sample. The level of Tα1 can be determined by immunoassays using anti-Tα1 peptide antibodies, for example. Other variations of such assays include radioimmunoassay (RIA), ELISA and immunofluorescence. Alternatively, nucleic acid probes can be used to detect and quantitate Tα1 peptide mRNA for the same purpose.

In another embodiment, the invention may provide a method for ameliorating a cell proliferative disorder assoicated with Tα1, including treating a subject having the disorder, at the site of the disorder, with a composition which regulates Tα1 activity. The term "ameliorate" denotes a lessening of the detrimental effect of the disease-inducing response in the patient receiving therapy. Where the disease is due to an overgrowth of cells, an antagonist of Tα1 peptide is effective in decreasing the amount of available Tα1. Such an antagonist may be a Tα1 specific antibody or functional fragments thereof (e.g., Fab, F(ab')$_2$). The treatment requires contacting the site of the disease with the antagonist.

The term "cell proliferative disorder", as used herein, refers to a condition characterized by abnormal cell growth. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. For example, Tα1 may be involved in a pathological condition by inducing a proliferative lesion in the intimal layer of an arterial wall, resulting in atherosclerosis. Instead of trying to reduce risk factors for the condition, e.g., lowering blood pressure or reducing elevated cholesterol levels, Tα1 peptide inhibitors or antagonists of the invention would be useful in interfering with the in vivo activity of Tα1 associated with atherosclerosis. Tα1 peptide antagonists are also useful in treating other disorders associated with an overgrowth of connective tissues, such as various fibrotic conditions, including scleroderma, arthritis and liver cirrhosis.

In yet another embodiment, the invention may provide a method of treating a subject having a cell proliferative disorder associated with Tα1 gene expression in a subject. The method includes administering to a subject having the disorder a therapeutically effective amount of an agent which modulates Tα1 gene expression, thereby treating the disorder. The term "modulate" refers to inhibition or suppression of Tα1 expression when Tα1 is overexpressed, and induction of expression when Tα1 is underexpressed. The term "therapeutically effective" means that amount of Tα1 agent which is effective in reducing the symptoms of the Tα1 associated cell proliferative disorder.

An agent which modulates Tα1 gene expression may be a polynucleotide for example. The polynucleotide may be an antisense, a triplex agent, or a ribozyme, as described above. For example, an antisense may be directed to the structural gene region or to the promoter region of Tα1.

Tα1 has been identified as a 28 amino acid peptide which results from the cleavage of the N-terminal region of prothymosin α1. Therefore, when a cell proliferative disorder is associated with the expression of Tα1, a therapeutic approach which directly interferes with the translation of prothymosin α1 messages into protein is possible. For example, antisense nucleic acid or ribozymes could be used to bind to the prothymosin α1 mRNA or to cleave it. Antisense RNA or DNA molecules bind specifically with a targeted gene's RNA message, interrupting the expression of that gene's protein product. The antisense binds to the messenger RNA forming a double stranded molecule which cannot be translated by the cell. Antisense oligonucleotides of about 15–25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. These and other uses of antisense methods to inhibit the in vitro translation of genes are well known in the art (Marcus-Sakura, *Anal., Biochem.,* 172:289, 1988).

Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target prothymosin α1 producing cell. The use of antisense methods to inhibit the in vitro translation of genes is well known in the art (Marcus-Sakura, *Anal.Biochem.,* 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.,* 1 (3):227, 1991; Helene, C., Anticancer Drug Design, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.,* 260:3030, 1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

These and other uses of antisense methods to inhibit the in vivo translation of genes are well known in the art (e.g., De Mesmaeker, et al., 1995. Backbone modifications in oligonucleotides and peptide nucleic acid systems. *Curr. Opin. Struct. Biol.* 5:343–355; Gewirtz, A. M., et al., 1996b. Facilitating delivery of antisense -oligodeoxynucleotides: Helping antisense deliver on its promise; *Proc. Natl. Acad. Sci. U.S.A.* 93:3161–3163; Stein, C. A. A discussion of G-tetrads 1996. Exploiting the potential of antisense: beyond phosphorothioate oligodeoxynucleotides. *Chem. and Biol.* 3:319–323).

Delivery of antisense, triplex agents, ribozymes, competitive inhibitors and the like can be achieved using a recombinant expression vector such as a chimeric virus or a colloidal dispersion system. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for antisense polynucleotides a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

The therapeutic agents useful in the method of the invention can be administered parenterally by injection or by gradual perfusion over time. Administration may be intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

The invention also includes a pharmaceutical composition comprising a therapeutically effective amount of $T\alpha 1$ in a pharmaceutically acceptable carrier. Such carriers include those listed above with reference to parenteral administration.

Antibodies that Bind to T=1

Antibodies to $T\alpha 1$ peptide or fragments could be valuable as diagnostic tools to aid in the detection of diseases in which $T\alpha 1$ is a pathological factor. Further, antibodies which bind to prothymosin $\alpha 1$ and inhibit or prevent the proteolytic cleavage of $T\alpha 1$ from promothymosin $\alpha 1$ are included in the present invention. Therapeutically, antibodies or fragments of the antibody molecule could also be used to neutralize the biological activity of $T\alpha 1$ in diseases where $T\alpha 1$ is inducing the overgrowth of tissue. Such antibodies can recognize an epitope of prothymosin $\alpha 1$, $T\alpha 1$, or fragments thereof, suitable for antibody recognition and neutralization of $T\alpha 1$ activity. As used in this invention, the term "epitope" refers to an antigenic determinant on an antigen, such as a $T\alpha 1$ peptide, to which the paratope of an antibody, such as an $T\alpha 1$-specific antibody, binds. Antigenic determinants usually consist of chemically active surface groupings of molecules, such as amino acids or sugar side chains, and can have specific three-dimensional structural characteristics, as well as specific charge characteristics.

Preparation of an antibody requires a substantially purified moiety that can provide an antigenic determinant. The term "substantially pure" as used herein refers to $T\alpha 1$, or variants thereof, which is substantially free of other proteins, lipids, carbohydrates or other materials with which it is naturally associated. Substantially purified or "isolated" refers to molecules, either nucleic or amino acid sequences, that are removed from their natural environment, isolated or separated, and are at least 60% free, preferably 75% free, and most preferably 90% free from other components with which they are naturally associated. One skilled in the art can isolate $T\alpha 1$ using standard techniques for protein purification. The substantially pure peptide will yield a single major band on a non-reducing polyacrylamide gel. The purity of the $T\alpha 1$ peptide can also be determined by amino-terminal amino acid sequence analysis. $T\alpha 1$ peptide includes functional fragments of the peptide, as long as the activity of $T\alpha 1$ remains. Smaller peptides containing the biological activity of $T\alpha 1$ are included in the invention. As used in the present invention, the term "antibody" includes, in addition to conventional antibodies, such protein fragments that have the ability to recognize specifically and bind the $T\alpha 1$ protein or variants thereof. Regions of the gene that differ at the protein level are well defined. A protein can be raised by expression of the wt gene or of the variants, or, preferably, fractions therefore. For example, the nucleic acid sequence can be cloned into expression vectors. According to this embodiment, the sequence of interest can first be obtained by employing PCR, as described above, or from a synthetic gene construction with overlapping and ligated synthetic oligonucleotides. Another alternative would involve synthesis of a short peptide. All those methodologies are well known to one skilled in the art. See, for example, Ausubel et al., CURRENT PROTOCOLS IN MOLECULAR BIOLOGY, Volumes 1 and 2 (1987), with supplements, and Maniatis et al., MOLECULAR CLONING, A LABORATORY MANUAL, Cold Spring Harbor Laboratory.

The genetic sequence discussed above then is expressed in any known, commercially available systems. Vectors for subcloning the sequence of interest, and subsequent expression into bacterial, yeast, baculovirus, insect, or tissue culture are well known to one skilled in the art. The subcloning process could, according to one embodiment, produce a fused protein with a short N- or C-terminal extension to facilitate subsequent purifications on columns or by use of antibodies. Alternatively, the protein of interest is purified by standard protein purification protocols. See for example PROTEIN PURIFICATION—PRINCIPLES AND PRACTICE, Springer Varlag publ., New-York; and PROTEIN BIOTECHNOLOGY, Humana Press, Totowa, N.J.

The preparation of polyclonal antibodies is well-known to those skilled in the art.

See, for example, Green et al., *Production of Polyclonal Antisera*, in IMMUNOCHEMICAL PROTOCOLS (Manson, ed.), pages 1–5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992), which are hereby incorporated by reference.

The preparation of monoclonal antibodies likewise is conventional. See, for example, Kohler & Milstein, *Nature* 256:495 (1975); Coligan et al., sections 2.5.1–2.6.7; and Harlow et al., ANTIBODIES: A LABORATORY MANUAL, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., *Purification of Immunoglobulin G* (IgG), in METHODS IN MOLECULAR BIOLOGY, VOL. 10, pages 79–104 (Humana Press 1992). Methods of in vitro and in vivo multiplication of monoclonal antibodies are well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

The invention provides a method for detecting $T\alpha 1$, or variants thereof, which includes contacting an anti-$T\alpha 1$ antibody with a cell or protein and detecting binding to the antibody. An antibody which binds to $T\alpha 1$ peptide is labeled with a compound which allows detection of binding to $T\alpha 1$. There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation. For purposes of the invention, an antibody specific for $T\alpha 1$ peptide may be used to detect the level of $T\alpha 1$ in biological fluids and tissues. Any specimen containing a detectable amount of antigen can be used. The level of $T\alpha 1$ in the suspect cell can be compared with the level in a normal cell to determine whether the subject is predisposed to a $T\alpha 1$ associated increase in angiogenesis.

The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the peptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

The invention includes antibodies immunoreactive with $T\alpha 1$ peptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., Nature, 256:495, 1975). The term antibody as used in this invention is meant to include intact molecules as well as fragments thereof, such as Fab and $F(ab')_2$, Fv and SCA fragments which are capable of binding an epitopic determinant on $T\alpha 1$.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An $(Fab')_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

Alternatively, a therapeutically or diagnostically useful anti-Tα1 antibody may be derived from a "humanized" monoclonal antibody. Humanized monoclonal antibodies are produced by transferring mouse complementary determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. USA* 86: 3833 (1989), which is hereby incorporate din its entirety by reference. Techniques for producing humanized monoclonal antibodies are described, for example, by Jones et al., *Nature* 321: 522 (1986); Riechmann et al., *Nature* 332: 323 (1988); Verhoeyen et al., *Science* 239: 1534 (1988); Carter et al., *Proc. Nat'l Acad Sci. USA* 89: 4285 (1992); Sandhu, *Crit. Rev. Biotech.* 12: 437 (1992); and Singer et al., *J. Immunol.* 150: 2844 (1993), which are hereby incorporated by reference.

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., *Ann. Rev. Immunol.* 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be sued to produce human antibody-secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6: 579 (1994), which are hereby incorporated by reference.

As is mentioned above, antigens that can be used in producing Tα1-specific antibodies include Tα1 peptides or Tα1 peptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

Modulation of Angiogenesis

Angiogenesis, a biological process that includes the proliferation and migration of endothelial cells, is defined as the growth of new blood vessels, in particular, capillaries and is an essential part of both normal and pathological tissue growth. Characteristic elements of angiogenesis include endothelial cell proliferation, endothelial cell migration, invasion of endothelial cells into tissues, and maturation of endothelial cells. Angiogenesis plays a crucial role in such beneficial functions as embryogenesis, wound healing and the female reproductive cycle, as well as in such abnormal functions as psoriasis, diabetic retinopathy, rheumatoid arthritis, hemangiomas, and solid tumor formation.

In another embodiment, the invention provides a method for modulating angiogenesis in a tissue including contacting the tissue with a therapeutically effective amount of a composition containing thymosin α1 peptide. It is envisioned that the method of the invention can be used to treat tissue damage in a subject after the tissue has been deprived of blood supply for a tissue damaging amount of time. The treatment can involve administering to the subject an effective amount of Tα1 peptide so as to contact the blood deprived tissue, thereby promoting angiogenesis in a tissue and treating or preventing tissue damage. For example, Tα1 peptide can be administered to prevent or treat tissue damage in cardiac tissue resulting from an incomplete or complete coronary occlusion by inducing angiogenesis and stimulating collateral circulation in the tissue affected by the occlusion. Thus, the method of the invention can be used restore blood flow to ischemic tissues thereby allowing nutrients and immunological factors access to the site of tissue damage.

In addition, the method of the invention is useful in promoting angiogenesis in tissues deprived of adequate blood flow. For example, a composition containing Tα1 can promote hair growth in a subject desiring such growth. One aspect of hair loss is the loss of vascularization in tissues containing hair follicles resulting in inadequate blood supplies to the hair follicle. A composition containing Tα1 can be applied to the affected area in an amount sufficient to cause neovascularization of the tissue resulting in hair growth.

Pathologically, Tα1 may be involved in diseases in which there is an overgrowth of blood vessels, such as cancer, tumor formation and growth, diabetic retinopathy, neovascular glaucoma, rheumatoid arthritis and psoriasis.

The ingrowth of capillaries and ancillary blood vessels is essential for growth of solid tumors and is thus an unwanted physiological response which facilitates the spread of malignant tissue and metastases. Inhibition of angiogenesis and the resultant growth of capillaries and blood vessels is therefore a component of effective treatment of malignancy in use for treatment of cancer patients.

Thus, in another embodiment, the invention may provide a method of inhibiting angiogenesis in a subject, including administering to the subject a composition containing an agent which regulates thymosin α1 activity. For example, the inhibition of angiogenesis and endothelial cell proliferation can be beneficial in controlling the growth of solid tumors. Most, if not all solid tumors, like normal tissue, require a steady and sufficient blood supply for optimal growth. Tumors are known to make use of angiogenic growth factors to attract new blood vessels and ascertain supply with sufficient amounts of nutrients to sustain their growth. Many tumors are well vascularized and the inhibition of the formation of an adequate blood supply to the tumor by inhibition of tumor vascularization, as a result of endothelial cell growth inhibition, is beneficial in tumor growth control. Without a strong blood supply, rapid and prolonged growth of tumor tissue cannot be sustained. Thus, agents which inhibit Tα1 activity may be used to prevent neoplastic growth. The Tα1 inhibiting agent may be administered orally, parenterally, topically, intravenously, or systemically. In addition, for inhibiting tumor cell proliferation and tumor growth, the agent may be administered locally directly to the tumor or as a part of a deposited slow release formulation. Administration may be on a daily basis for as long as needed to inhibit angiogenesis, endothelial cell proliferation, tumor cell proliferation or tumor growth. Alternatively, a slow release formulation may continue for as long as needed to control tumor growth. This dosage regimen may be adjusted to provide the optimum therapeutic response. For example, several divided doses may be administered daily or the dose may be proportionally reduced as indicated by the exigencies of the therapeutic situation.

In this regard, the compositions of this invention that are useful as inhibitors of angiogenesis, endothelial cell proliferation, tumor cell proliferation and tumor growth contain a pharmaceutically acceptable carrier and an amount of Tα1 modulating agent effective to inhibit tumor or endothelial cell proliferation. Such compositions may also include preservatives, antioxidants, immunosuppressants and other biologically and pharmaceutically effective agents which do not exert a detrimental effect on the Tα1 modulating agent. For treatment of tumor cells, the composition may include a chemotherapeutic agent, for example an anti-cancer agent which selectively kills the faster replicating tumor cells, many of which are known and clinically used. Exemplary anti-cancer agents include melphalan, cyclophosphamide, methotrexate, adriamycin and bleomycin.

Modulation of Monocyte Chemotaxis

Monocytes or (i.e., mononuclear phagocytes) are incompletely differentiated phagocytic white blood cells which circulate in the blood. Monocytes settle in tissues and mature into tissue macrophages. Circulating monocytes are involved in clearing antigen/antibody complexes from the circulation. Migration of monocytes from blood vessels in to distressed or damaged tissues is crucial to the initiation of normal disease fighting inflammatory responses. Thus, in another embodiment, the invention provides a method of modulating monocyte migration including contacting the monocyte with a migration inducing effective amount of thymosin α1 peptide. Thus, Tα1 is useful for attracting monocytes to the site of damaged and/or infected tissues for the purpose of preventing or ameliorating disease states associated with viral or bacterial infections. Previously disclosed methods for applying compositions containing Tα1 to a site in need of such treatment can be used to promote the prevention or treatment of an infection.

Monocyte recruitment is also involved in the onset and progression of debilitating and life-threatening inflammatory and autoimmune diseases. The pathology of these diseases results from the attack of the body's immune system defenses on normal tissues. Thus, in another aspect of the invention, agents which modulate the activity of Tα1 can be used to prevent or ameliorate a disease state associated with inflammatory and autoimmune diseases. These disease include, but are not limited to, rheumatoid arthritis, psoriasis, contact dermatitis, inflammatory bowel disease, multiple sclerosis, atherosclerosis, sarcoidosis, idiopathic pulmonary fibrosis, dermatomyositis, hepatitis, diabetes, allograft rejection and graft-vs-host disease.

Screen for compounds which modulate Tα1 activity

In another embodiment, the invention provides a method for identifying a compound which modulates Tα1 cell migration activity, angiogenesis activity or wound healing activity. The method includes: a) incubating components comprising the compound and Tα1 under conditions sufficient to allow the components to interact; and b) determining the effect of the compound on Tα1 activity before and after incubating in the presence of the compound. Compounds that affect Tα1 activity (e.g., antagonists and agonists) include peptides, peptidomimetics, polypeptides, chemical compounds and biologic agents. Tα1 activity can be assayed using methodology as described in the present Examples.

Further, the method includes determining whether a compound has an effect on production of Tα1 from prothymosin. Prothymosin can be analyzed before and after incubation to determine, for example, if the compound inhibits production of Tα1. If a compound inhibits the production of Tα1, only prothymosin, or a predominant amount of prothymosin will remain in the test sample. Alternatively, if the compound stimulates production of Tα1 from prothymosin, less prothymosin and more Tα1 will be present in the test sample after incubation. The amino acid sequence can be determined by standard N-terminal sequencing methods or by contacting the sample with a monoclonal antibody which distinguishes between prothymosin and Tα1.

Incubating includes conditions which allow contact between the test compound and the Tα1 or prothymosin. Contacting includes in solution and in solid phase, or in a cell. The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Cell Culture

Human umbilical vein endothelial cells (HUVECs) were isolated from freshly delivered cords according to Jaffe et al. (*J. Clin. Invest.* 52: 2745, 1973) and grown on Nunclon dishes (Nunc, Denmark) in RPMI 1640 (Life Technologies, Gaithersburg, Md.) supplemented with 20% bovine calf serum (Hyclone Laboratories, Logan Utah), 100 U/ml penicillin/streptomycin (Life Technologies, Gaithersburg, Md.), 50 µg/ml gentamycin (Life Technologies, Gaithersburg, Md.), 2.7 µg/ml amphotericin B (fungizone) (Life Technologies, Gaithersburg, Md.), 5 U/ml sodium heparin (Fisher Scientific, Pittsburgh, Pa.) and 200 µg/ml endothelial cell growth supplement (ECGS) (Collaborative Research, Bedford, Mass.). Cells between passage 3 and 5 were used for all experiments. Human coronary artery endothelial cells (HCAECs) were grown on Nunclon dishes in the HUVEC media. Foreskin fibroblasts (Ffs) were grown in DMEM supplemented with 10% fetal bovine serum (Hyclone) on Falcon (Becton Dickinson, N.J.) dishes. HT1080 cells (human fibrosarcoma cell line) were grown in Falcon flasks in DMEM supplemented with 10% fetal bovine serum. Neutrophils were freshly isolated from buffy coats as previously reported (Kibbey et al., *J. Cell Phys.* 160:185, 1994). Human aortic smooth muscle cells (AOSMCs) were grown in smooth muscle cell media (Clonetics, San Diego, Calif.) on Nunclon dishes.

EXAMPLE 2

Tube formation is enhanced in the presence of Tα1

Migration and differentiation during angiogenesis can be studied in vitro using Matrigel, a basement membrane matrix on which HUVECs undergo capillary-like tube formation (Grant et al., *J. Cell. Physiol.* 153: 614, 1992; Kubota et al., *J. Cell Biol.* 107: 1589, 1988). The tube formation assay was performed according to Grant et al. (*J. Cell. Physiol.* 153:614, 1992) with the following modifications. Twenty-four well Nunclon plates were coated with 320 μl of Matrigel (10 mg/ml) and incubated at 37° C. for 30 min to promote gelling. 30,000 HUVECs were resuspended in growth media and added to each well with 1, 10, 100 and 1000 ng of synthetic Tα1, 20 and 200 μg/ml ECGS (a bovine brain extract that contains aFGF and bFGF and acts as a positive control) or media alone. The final serum concentrations were 10% or 5%. After 18 h, plates were fixed with Diff-Quik (Baxter Healthcare Corporation, McGraw Park, Ill.) and the length of the tubes was measured using an Olympus CK2 microscope with a 2x objective connected to a Javelin CCTV camera with a 3.3x coupler and NIH Image 1.57 software. Three random measurements of each of four wells at each culture condition were measured. Each experiment was repeated at least three times.

Figure 1:
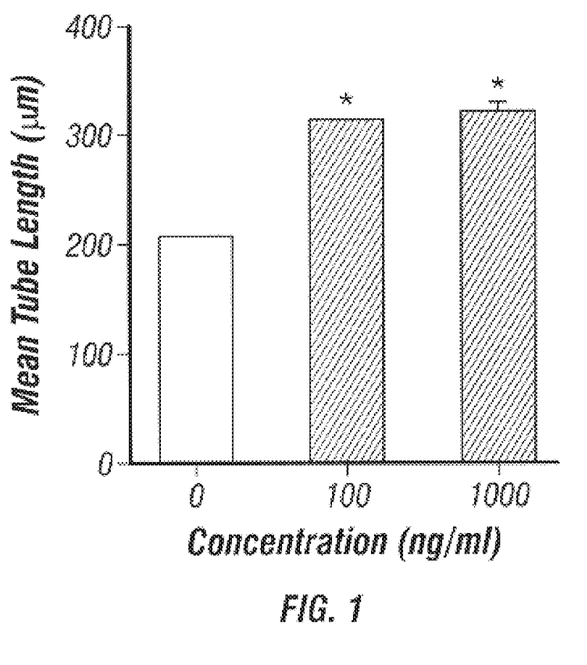
FIG. 1 is a bar graph which shows the effect of Tα1 on human umbilical vein epithelial cell (HUVEC) differentiation on Matrigel by indicating the difference in tube length between cells cultured in media alone containing 10% serum compared to those cultured with 100 or 1000 ng/ml Tα1. Data points represent the average length of tubes in pixels of three random fields of quadruplicate wells±SEM. *P<0.0001, significantly different from media alone (Welch's t-test).
Figure 2A:
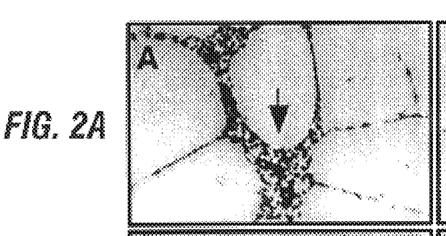
FIG. 2A shows examples of tubes formed in the absence of Tα1 in the presence of media alone containing 10% serum. Note that tubes that form without Tα1 contain large areas of flattened cells (arrow).
Figure 2B:
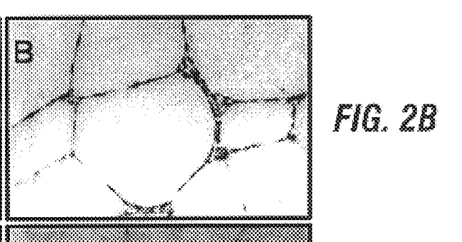
FIG. 2B shows tubes that formed in the presence of 1000 ng/ml Tα1 and 10% serum containing media.
Figure 2C:
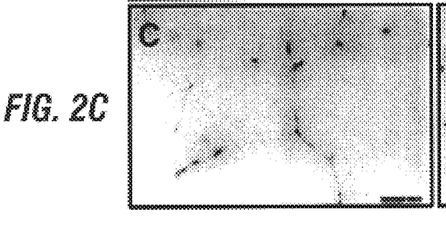
FIG. 2C shows examples of tubes formed in the absence of Tα1 in the presence of media alone containing 5% serum. Bar=100 Mm.
Figure 2D:
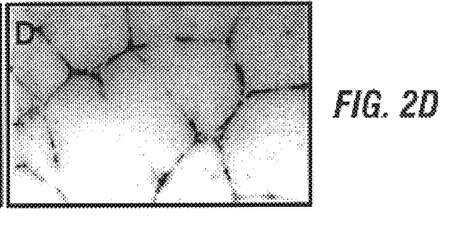
FIG. 2D shows tubes formed in the presence of 1000 ng/ml of Tα1 and 5% serum containing media.

When 10% serum was used, cells incubated with 100 or 1000 ng/ml Tα1 formed more tubes than control cells (FIG. 2B). The tubes were significantly longer (P≦0.0001) with an average length of 316–324 μm compared to cells in media alone that formed tubes 208 μm long (FIG. 1) and had large numbers of unorganized cells (FIG. 2A, arrow). When placed in media with 5% serum (FIG. 2C), in media alone or in 1 or 10 ng/ml Tα1, cells did not form tubes while those incubated with 100 and 1000 ng/ml Tα1 formed highly organized tubes (FIG. 2D).

EXAMPLE 3

Migration effects are cell type specific

Several cell types were tested to determine if the migratory stimulation observed with Tα1 was specific. Foreskin fibroblasts, neutrophils, HT1080 fibrosarcoma cells, and human aortic smooth muscle cells did not demonstrate any significant migration toward Tα1 (Table 1). HUVEC migration assays were carried out in Boyden chambers using 12 ,m pore PVP free filters coated with either a 0.1 mg/ml or 0.05 mg/ml solution of collagen IV as previously reported (Malinda et al., *FASEB J.* 11:474, 1997). Each condition was assayed in triplicate wells at least three times unless indicated. HCAECs, AOSMCs, FFs, HT1080 cells and neutrophils were cultured or isolated and assayed for migration as previously reported (Malinda et al., *FASEB J.* 11:474, 1997).

The cells migrated toward their respective positive controls. In contrast, human coronary artery endothelial cells migrated to Tα1 with a 2-fold increase (P<0.0001) in migration over media alone in response to 1000 ng of Tα1 (Table 1). Significant migration was also observed with 1–100 ng doses (P<0.0001) showing that the response to Tα1 could occur in other endothelial cell types. Monocyte migration was stimulated by Tα1 similar to the positive control. Monocyte migration increased in response to 1000 ng/ml of Tα1 (P=0.003), while migration appeared to be inhibited by 100 ng/ml. Higher levels of Tα1 may trigger migration similar to an inflammatory response when the cells invade surrounding tissues and the inhibitory response to lower levels of Tα1 could be due to cell activation. Therefore, Tα1 specifically stimulates endothelial cell and monocyte migration.

EXAMPLE 4

In vitro "scratch" wound closure is more rapid in the presence of Tα1

During angiogenesis the cells may be presented with a constant level of Tα1. The "scratch" wound closure assay was used to assess the potential effects of constant doses of Tα1 on cell migration. Confluent monolayers were "scratch" wounded using the tip of a universal blue pipette tip and rinsed with PBS. Tα1 (1, 10, 100, and 1000 ng/ml) or ECGS (200 μg/ml) was added to the wells in fresh media lacking ECGS but containing 10 mM thymidine to inhibit cell proliferation (Malinda et al., *FASEB J.* 11: 474, 1997). Antibody inhibition experiments were carried out as described above by wounding the cell monolayer and then adding either anti-Tα1 polyclonal antibody (1/25, 1/50 dilution) or pre-immune serum (1/25 dilution), or fresh media to the plate.

Figure 3A:
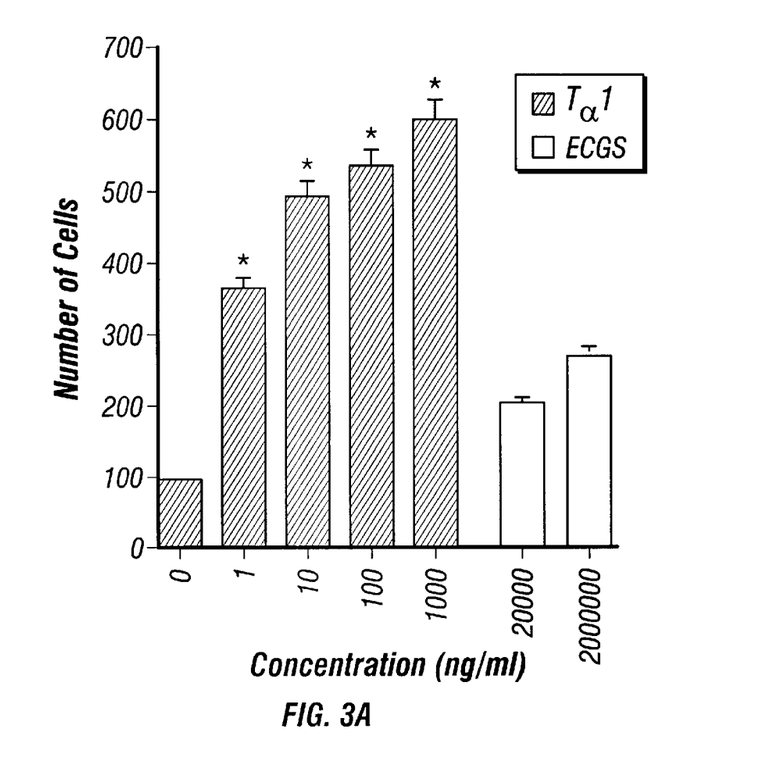
FIG. 3A is a bar graph which shows Tα1 stimulated HUVEC migration in Boyden chamber assays. Tα1 in the lower wells of the chamber resulted in a 3–6 fold increase in migration on filters coated with collagen IV. The positive control, ECGS, also showed increased migration over media alone.
Figure 3B:
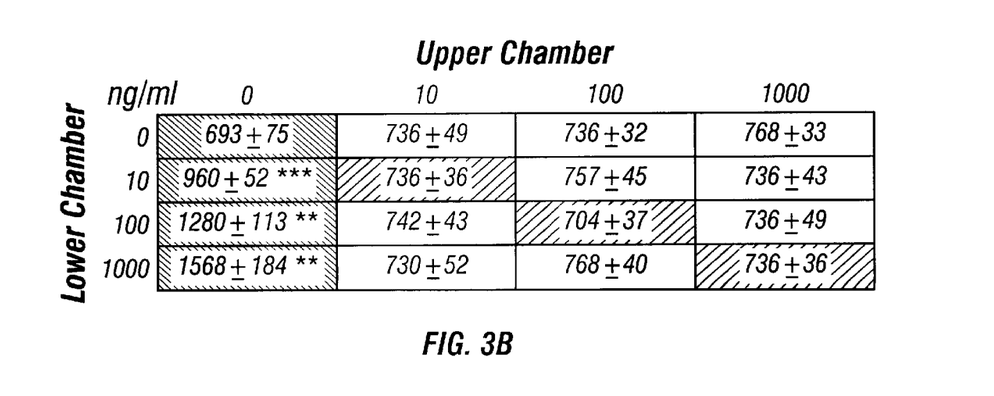
FIG. 3B shows results from a checkerboard assay containing increasing concentrations of Tα1 in the lower well (dark gray shading=migration due to chemoattraction) and increasing concentrations of Tα1 in upper and lower wells (light gray shading=migration due to chemokinesis). More cells migrated along the concentration gradient of Tα1 in the lower well (dark gray=chemoattraction). This result is the average of three experiments. Data points are expressed as the number of migrated cells±SEM. *P<0.0001, P=0.001, *P=0.01 (for A) or P=0.03 (for B), significant difference from media alone (Student's t-test).

Migration of cells into the wounded area was significantly increased in the presence of 1000 ng/ml of Tα1 (P<0.0001) over migration in the presence of media alone within 2 h after wounding (14% closure vs 1%) (FIG. 3A and FIG. 3B). Wound closure was similar to that in the presence of the positive control, ECGS, and remained elevated throughout the 10 h experiment. Acceleration of wound closure was also observed in response to 100 ng/ml Tα1 as early as 2 h (7% vs 1%, P<0.0001). When wounded monolayers were incubated in the presence of Tα1 antibody, wound closure was inhibited 1.6-fold compared to that observed in the presence of media alone (P≦0.0001). Pre-immune sera had no effect on cell migration and there was no indication of altered cell morphology or death of the anti-Tα1-treated cells. Antibody reduction of the levels of Tα1, therefore, altered HUVEC migration.

EXAMPLE 5

In vivo endothelial cell migration and vessel formation are enhanced by Tα1

Figure 4:
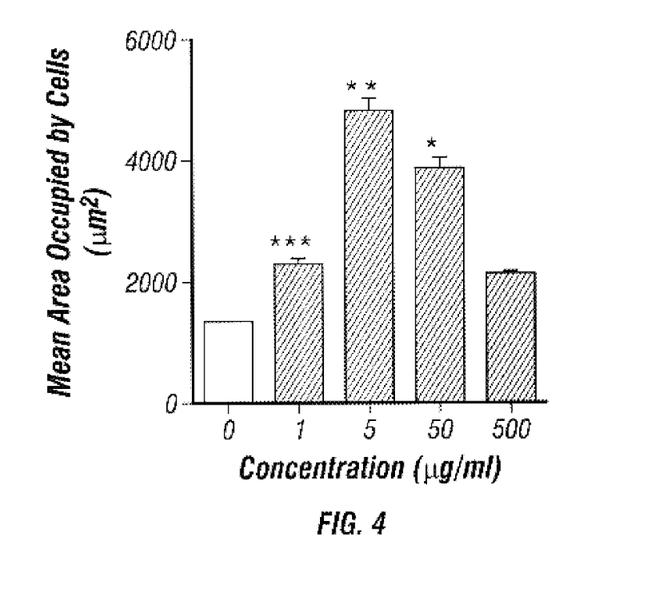
FIG. 4 shows a bar graph of Tα1 induced increase in cell migration and angiogenesis in vivo in the subcutaneous Matrigel plug assay. Three experiments expressed as the mean area occupied by cells $(\mu m^2) \pm SEM$. *P<0.0001, P=0.0007, *P=0.03 (Welch's t-test).
Figure 5A:
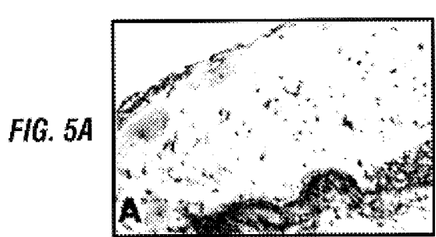
FIG. 5A is a negative control showing Matrigel in the absence of Tα1. There was a low level of cell migration or angiogenesis in vivo in the subcutaneous Matrigel plug assay. Masson's trichrome stains Matrigel blue and endothelial cells red. The side underlying the skin is at the top of the figure.
Figure 5B:
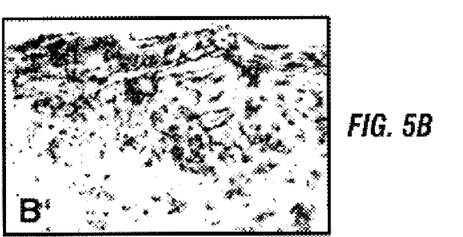
FIG. 5B shows a positive control of endothelial cell growth supplement (ECGS) (10 ng/ml) induced increase in cell migration and angiogenesis in vivo in the subcutaneous Matrigel plug assay. Masson's trichrome stains Matrigel blue and endothelial cells red. The side underlying the skin is at the top of the figure.
Figure 5C:
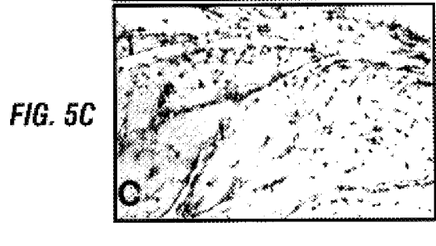
FIGS. 5C and 5D show that 5 $\mu$g/ml of Tα1 induced a increase fold in cell migration and angiogenesis in vivo in the subcutaneous Matrigel plug assay. Masson's trichrome stains Matrigel blue and endothelial cells red. The side underlying the skin is at the top of the figure. The Response to Tα1 is variable but always significantly higher than Matrigel alone Bar=100 $\mu$m.
Figure 5D:
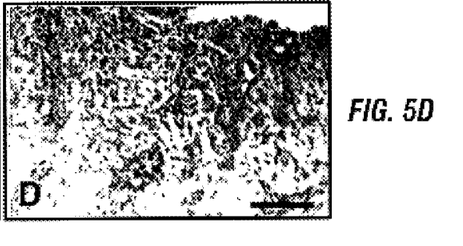

Since Tα1 enhanced HUVEC migration in vitro, experiments were performed to determine if Tα1 promoted cell migration and vessel formation in vivo. Endothelial cells invade and form vessels in Matrigel plugs containing angiogenic factors (Kibbey et al., *J. Cell Phys.* 160:185, 1994; Passaniti et al., *Lab. Invest.* 67: 519, 1992). Matrigel was mixed with Tα1 (5, 50 and 500 μg/ml) or ECGS (10 and 100 ng/ml) and injected subcutaneously into three or four C57Bl/6N female mice for each condition (Malinda et al., *FASEB J.* 11:474, 1997). Three random fields were collected and analyzed per plug in each of three experiments. Matrigel plugs containing 5 or 50 μg/ml of Tα1 showed a significant 3- to 3.7-fold increase (P<0.0001, P=0.001 respectively) in the number of cells in the plugs compared to plugs containing Matrigel alone (FIG. 4). At the lower and higher concentrations, 1 μg/ml and 500 μg/ml, a decrease in migration was observed. Cells migrate into the plug from the area closest to the skin forming vessels (FIG. 5). Plugs containing Tα1 (FIGS. 5C and 5D) show many more cells than in the Matrigel alone (FIG. 5A). Cell morphology was similar to those in plugs containing 10 ng/ml of the positive control ECGS (FIG. 5B). These results indicate that Tα1 is a potent cell migration and vessel formation factor in vivo.

EXAMPLE 6

In vivo wound healing is accelerated by Tα1

Figure 6A:
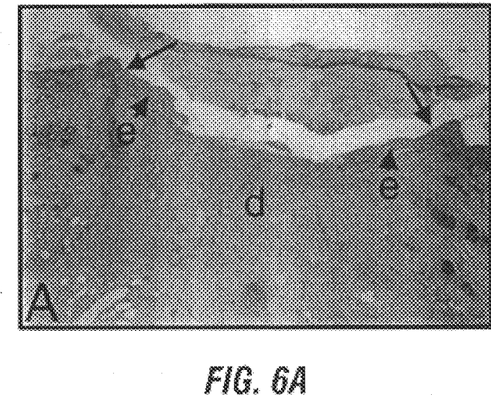
FIG. 6A shows hematoxylin and eosin stained sections of 8 day punch wounds in the absence of Tα1 with epithelial loss and adjacent focally extensive layer of neutrophils/eosinophils. Epithelial migration and hyperplasic epithelium are visible adjacent to the wound (4×). Arrows indicate the tissue undergoing repair. e=epidermis; d=dermis; c=capillaries.
Figure 6B:
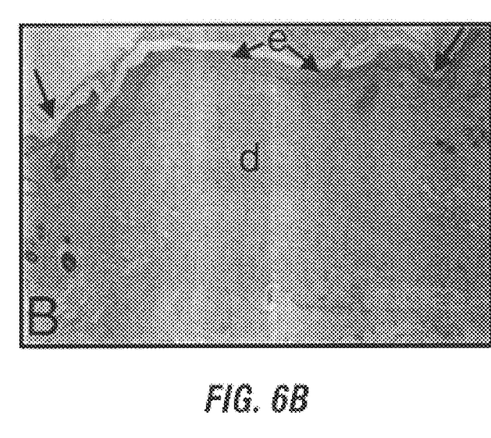
FIG. 6B shows hematoxylin and eosin stained sections of 8 day punch wounds in the presence of Tα1. Complete reepithelization of the wound occurred when Tα1 was injected intraperitoneally on alternate days (60 $\mu$g/300 $\mu$l). Granulation tissue is infiltrated with a large number of cells and a moderate number of vessels (4×). Arrows indicate the tissue undergoing repair. e=epidermis; d=dermis; c=capillaries.
Figure 6C:
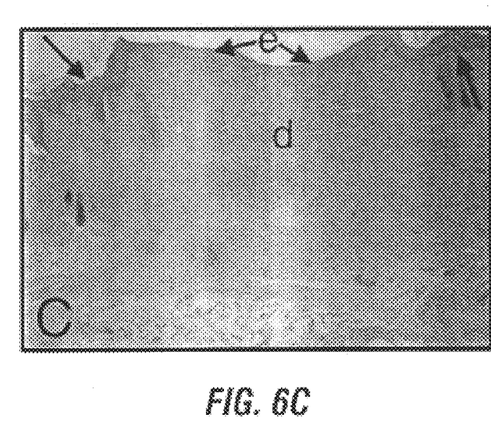
FIG. 6C shows hematoxylin and eosin stained sections of 8 day punch wounds in the presence of Tα1. Tα1 topical treatment (5 $\mu$g/50 $\mu$l) results in complete reepithelization of the wound with 2–3 layers of thick epidermis. Dermal areas show granulation tissue infiltrated with fibroblasts and extensive neovascularization (4×). Arrows indicate the tissue undergoing repair. e=epidermis; d=dermis; c=capillaries.

Tα1, whether administered topically or intraperitoneal, significantly accelerated wound healing as compared to untreated wounds (FIG. 6A vs 6B, and 6C). Six full thickness 8 mm punch biopsy wounds were made on the dorsal surface of rats as previously reported (Bhartiya et al., *J. Cell. Physiol.* 150:312, 1992; Sihhu et al., *J. Cell. Physiol.* 169:108, 1996) and Tα1 was given topically at the time of wounding (5 μg in 50 μl) and again after 48 hr. Controls for the topical treatment received identical amounts of saline at the time of wounding and at 48 hr. Three rats in each group also received intraperitoneal injections at the time of wounding (60 μg in 300 μl) and again every other day. Controls for these animals received identical amounts of saline i.p. on the same injection schedule. At days 8 and 9 post-wounding, tissue was collected and fixed in 10% buffered formalin (i.p. n=18 samples; topical n=9 samples). The samples were sectioned and stained with H&E and Masson's Trichrome (American Histolabs, Gaithersburg, Md.).

Figure 6D:
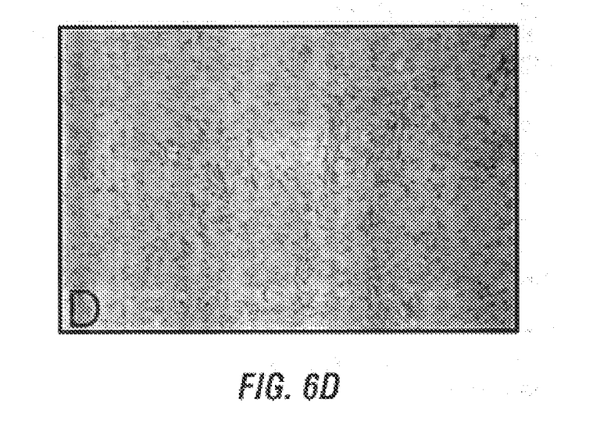
FIG. 6D shows hematoxylin and eosin stained sections of 8 day punch wounds in the absence of Tα1. There are few cells near the dermis and little neovascularization near the dermal and epidermal junction (20×). e=epidermis; d=dermis; c=capillaries
Figure 6E:
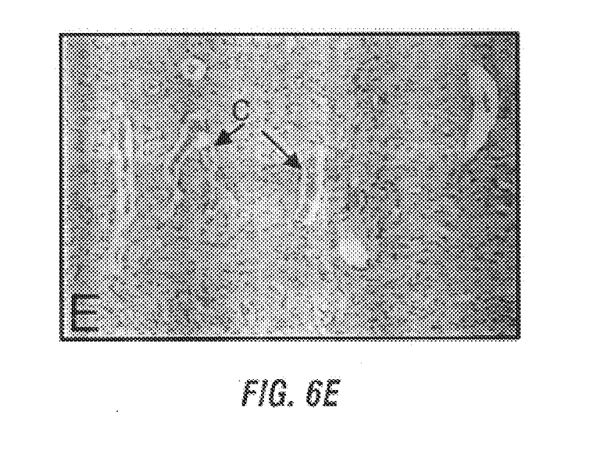
FIG. 6E shows hematoxylin and eosin stained sections of 8 day punch wounds in the dermis near the dermal and epidermal junction (20×) in the presence of Tα1. Intra-peritoneal treatment with Tα1 resulted in capillary ingrowth in granulation tissue and hypercellular dermis as compared to FIG. 6D. Arrows indicate the tissue undergoing repair. e=epidermis; d=dermis; c=capillaries.
Figure 6F:
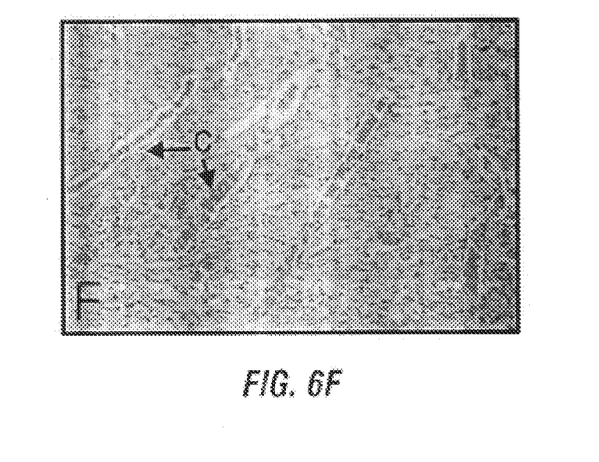
FIG. 6F shows hematoxylin and eosin stained sections of 8 day punch wounds in the dermis near the dermal and epidermal junction (20×) in the presence of Tα1. Topical application of Tα1 resulted in capillary ingrowth in granulation tissue and hypercellular dermis as compared to FIG. 6D. Arrows indicate the tissue undergoing repair. e=epidermis; d=dermis; c=capillaries.
Figure 6G:
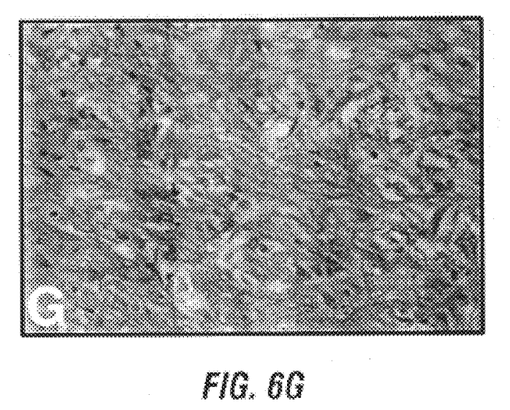
FIG. 6G shows Masson's trichrome stained sections of 8 day punch wounds in the absence of Tα1. Masson's trichrome staining indicates collagen in blue and endothelial cells in red (40×). Arrows indicate the tissue undergoing repair. e=epidermis; d=dermis; c=capillaries.
Figure 6H:
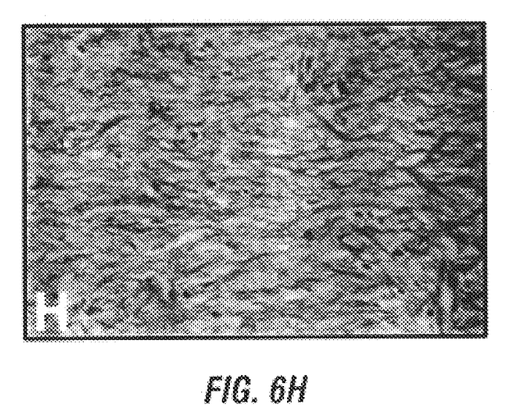
FIG. 6H shows Masson's trichrome stained sections of 8 day punch wounds in the presence of Tα1. Masson's trichrome staining indicates collagen in blue and endothelial cells in red (40×). Intraperitoneal introduction of Tα1 enhanced collagen production as compared to the untreated wounds shown in FIG. 5G. Arrows indicate the tissue undergoing repair. e=epidermis; d=dermis; c=capillaries.
Figure 6I:
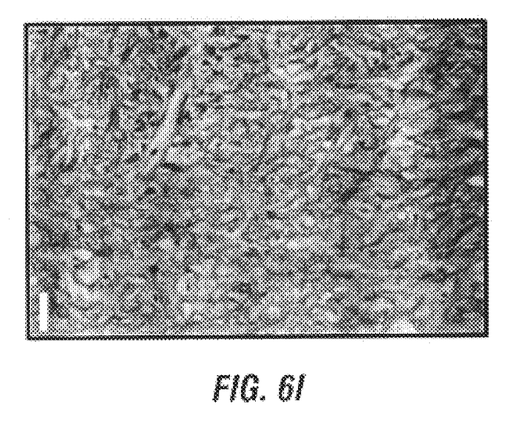
FIG. 6I shows Masson's trichrome stained sections of 8 day punch wounds in the presence of Tα1. Masson's trichrome staining indicates collagen in blue and endothelial cells in red (40×). Topical application of Tα1 enhanced collagen production as compared to the untreated wounds shown in FIG. 6G. Arrows indicate the tissue undergoing repair. e=epidermis; d=dermis; c=capillaries.

Migration of cells into the granulation tissue and complete reepithelization of the epithelium were observed (FIGS. 6B and 6C). Tα1 treatment by both methods resulted in considerable capillary ingrowth especially, when applied topically (FIG. 6D vs 6E and 6F). These results suggest that Tα1 is active in vivo for the formation of granulation tissue by promoting cell proliferation, migration and vessel formation. Additionally, an increase in the accumulation/biosynthesis of collagen by Tα1 treated wounds as compared to the untreated control (FIG. 6G vs 6H and 6I) suggests a role for Tα1 in wound contraction (Kirsner et al., *Dermatologic Clinics* 11:629, 1993).

The invention now being fully described, it will be apparent to one of ordinary skill in the art that many changes and modifications can be made thereto without departing from the spirit or scope of the appended claims.

TABLE 1

Response of Different Cell Types to $T\alpha_1$

| Cell Type | Thymosin $\alpha_1$ (ng/ml) | | | | | Positive Control |
|---|---|---|---|---|---|---|
| | 1000 | 100 | 10 | 1 | 0 | |
| FF | 5.2 ± 0.5 | 4.8 ± 0.7 | 5 ± 0.4 | 5 ± 0.4 | 5 ± 0.3 | bFGF (10 ng/ml) = 12.3 ± 0.3* |
| AOSMC | 1 ± 0.4 | 0.5 ± 0.5 | 1 ± 0.4 | 1 ± 0.3 | 0.9 ± 0.3 | PDGF-BB (10 ng/ml) = 36 ± 4.5* |
| Neutrophils | 149.3 ± 27 | 149.3 ± 13.5 | 138.7 ± 20 | 138.7 ± 12.8 | 149.3 ± 12 | FMLP ($10^{-7}$M) = 1404.7 ± 58.2* |
| Monocytes | 80 ± 7.6** | 20 ± 5.4** | N.D. | N.D. | 49 ± 8.1 | FMLP ($10^{-7}$M) = 74 ± 2.1** |
| HCAEC | 21 ± 0.4** | 18 ± 0.4* | 16 ± 0.5* | 14 ± 0.3* | 11 ± 0.3 | ECGS (200 ug/ml) = 19 ± 0.2* |
| HT1080 | 0.9 ± 0.4 | 1.3 ± 0.7 | 1.8 ± 0.4 | 2.4 ± 0.8 | 2.0 ± 0.5 | LN (1 ug/ml) = 661.2 ± 37* LN (5 ug/ml) = 1136 ± 70.3* |

N.D.: not done,
FF: foreskin fibroblasts,
AOSMC: human aortic smooth muscle cells,
HCAEC: human coronary hartery endothelial cells
HT 1080: human fibrosarcoma cell line,
bFGF: basic fibroblast growth factor,
PDGF-BB: platelet derived growth factor B form,
ECGS: endothelial cell growth supplement,
LN: laminin.
Numbers represent the average number of cells that migrated ± SEM in Boyden chamber assays.
*P ≤ 0.0001,
**P = 0.003, significant difference from media alone (Student's t-test).

What is claimed is:

1. A method for accelerating wound healing in a subject having a wound comprising contacting the site of the wound with a therapeutically effective amount of a composition containing thymosin α1 peptide.

2. The method of claim 1, wherein the composition further contains an agent that stimulates the production of thymosin α1 peptide.

3. The method of claim 1, further comprising contacting the site of the wound with an agent other than thymosin α1 which promotes wound healing.

4. The method of claim 3, wherein the agent is transforming growth factor beta (TGF-β).

5. A method for modulating angiogenesis in a tissue in need of such modulating comprising contacting the tissue with a therapeutically effective amount of a composition containing thymosin α1 peptide.

6. The method of claim 5, wherein the contacting is in vivo in a subject.

7. A method for modulating angiogenesis in a tissue comprising contacting the tissue ex vivo with a therapeutically effective amount of a composition containing thymosin α1 peptide.

8. The method of claim 5, wherein angiogenesis is accelerated.

9. The method of claim 6, wherein the subject is a mammal.

10. The method of claim 9, wherein the mammal is human.

11. A method for modulating angiogenesis in a tissue comprising contacting the tissue with a therapeutically effective amount of a composition containing thymosin α1 peptide and an agent that stimulates the production of thymosin α1.

12. A method for modulating angiogenesis in a tissue comprising contacting the tissue with a therapeutically effective amount of a composition containing thymosin α1 peptide and an agent other than thymosin α1 which promotes angiogenesis.

13. The method of claim 12, wherein the agent is transforming growth factor beta (TGF-β).

14. The method of claim 3, wherein the agent is a growth factor.

15. The method of claim 12, wherein the agent is a growth factor.

16. A pharmaceutical composition comprising thymosin α1 in an amount sufficient to promote wound healing, in a pharmaceutically acceptable carrier and transforming growth factor beta (TGF-β).

* * * * *